US00PP14431P39

(12) United States Plant Patent
Stribling

(10) Patent No.: US PP14,431 P3
(45) Date of Patent: Dec. 30, 2003

(54) SCHEFFLERA PLANT NAMED 'DAZZLE'

(50) Latin Name: *Schefflera arboricola*
Varietal Denomination: Dazzle

(75) Inventor: Sally L. Stribling, Homestead, FL (US)

(73) Assignee: Miami Agra Starts, Inc., Homestead, FL (US)

( * ) Notice: Subject to any disclaimer, the term of this patent is extended or adjusted under 35 U.S.C. 154(b) by 0 days.

(21) Appl. No.: 10/091,512

(22) Filed: Mar. 7, 2002

(65) Prior Publication Data

US 2003/0172427 P1 Sep. 11, 2003

(51) Int. Cl.[7] ..... A01H 5/00

(52) U.S. Cl. ..... Plt./377

(58) Field of Search ..... Plt./377

*Primary Examiner*—Kent Bell

(74) *Attorney, Agent, or Firm*—Foley & Lardner

(57) ABSTRACT

A new and distinct cultivar of *Schefflera arboricola* named 'Dazzle' as shown and described, and particularly characterized by the uniqueness of combined characteristics of heavily variegated foliage, large oblanceolate-shaped leaflets with a cuspidate tip approximately 15–20 centimeters in diameter.

2 Drawing Sheets

Latin name of the genus and species of the plant claimed: *Schefflera arboricola.*
Variety denomination: 'Dazzle'.

BACKGROUND OF THE INVENTION

The present invention comprises a new and distinct cultivar of Schefflera plant, hereinafter referred to by the cultivar name 'Dazzle'. 'Dazzle' is a sport mutation from an unnamed cultivar of *Schefflera arboricola.*

The new cultivar was discovered by the inventor, Sally L. Stribling, in Homestead, Fla. as part of a controlled breeding program of *Schefflera arboricola*, as a naturally occurring sport mutation. The mutation was observed as a single branch growing on the unnamed parent cultivar (unpatented). The mutated branch was propagated by peat media stem cuttings in Homestead, Fla. under mist in a greenhouse.

The new characteristics of the new cultivar 'Dazzle' have remained constant through successive generations and the new cultivar reproduces true to type. Asexual reproduction, by vegetative cutting and airlayering, through succeeding generations has established that the combination of characteristics as herein disclosed for the new cultivar are firmly fixed and retained through successive generations of asexual reproduction. The new invention differs substantially from the parent cultivar in leaf size, shape and leaf color.

BRIEF SUMMARY OF THE INVENTION

The new cultivar differs from the parent plant in that the leaves are larger than those of the parent plant.

The leaves of the new cultivar like those of the parent plant are smooth edged and are lacking serration. The new cultivar's leaflet is oblanceolate where the parent plant's leaflet shape is more obovate with an acuminate tip. Additionally the new cultivar has heavily variegated leaf coloration where the parent plant has no variegation.

No claims are made particularly to insect or disease resistance. The new cultivar is susceptible to aphids, scales and spider mites to a similar degree as is the parent plant.

To date the new cultivar 'Dazzle' has not born seed or fruit. *S. arboricola* (parent) generally bear seed after three years but the asexually propagated new cultivar dazzle has only been cultured to date for 18 months.

'Dazzle' has not been observed under all possible environmental conditions. The phenotypic expression may vary with variations in environment such as temperature, light intensity, day length and cultural conditions, without a change in the genotype of the plant.

BRIEF DESCRIPTION OF THE DRAWING

The accompanying photographic drawings illustrate the new cultivar at one year and show colors as true as is reasonably possible in reproductions of this type.

Sheet one depicts a side view of a typical mature specimen of the new cultivar 'Dazzle' that has been grown trellised in a shadehouse in Homestead, Fla. under 72% shade during the months of January 2001 through December 2001.

Sheet two depicts a close-up view of typical leaves and leaflets of the new cultivar 'Dazzle'.

DETAILED BOTANICAL DESCRIPTION

In this description, color references are to The Royal Horticultural Society Colour Chart (R.H.S.). The color references are approximate as color depends to a degree on horticultural practices such as light level and fertilization rates. The plant described is one year old and was grown in Homestead, Fla. in a shadehouse.

Foliage:

*Leaf type and shape.*—Radially compound leaves.
*Leaflet.*—Oblanceolate with a cuspidate tip.

*Average leaf size.*—15–20 cm in diameter, with approximately 8 leaflets per leaf measuring approximately 10 cm long and 5 cm wide.

*Leaf texture.*—Leathery, thick, smooth and glabrous.

*Petioles.*—Average length 20 cm, color RHS 144B.

*Color of upper surface of foliage.*—Heavily variegated coloration irregularly patterned, yellow-green RHS 147 A, green 139 A, yellow 11 B, gray 194 A.

*Color of lower surface of foliage.*—Mottled irregular variegation of green RHS 138 A and yellow-green RHS 144 C.

*Stem color.*—Older mature stem: RHS 144 A. Juvenile stem: RHS 144 B.

*Stem size.*—1.80 meters in length, 12 mm diameter.

*Internode length.*—2.5–4 cm.

*Leaflets per rack.*—Approximately 8.

Plant:

*Growth habit.*—Upright, bushy, and full. Removal of terminal apices enhances branching.

*Plant height.*—(as depicted in the first drawing): 180 cm at 1 year old from three rooted cuttings originally measuring 12 cm.

*Plant diameter.*—50 cm at the base, 51 cm at the apex.

*Plant vigor.*—Moderate, growth of 15 cm a month.

Flower description: Flowers have not been observed on plants of the new Schefflera.

I claim:

1. A new and distinct cultivar of *Schefflera arboricola* plant named 'Dazzle' as herein shown and described.

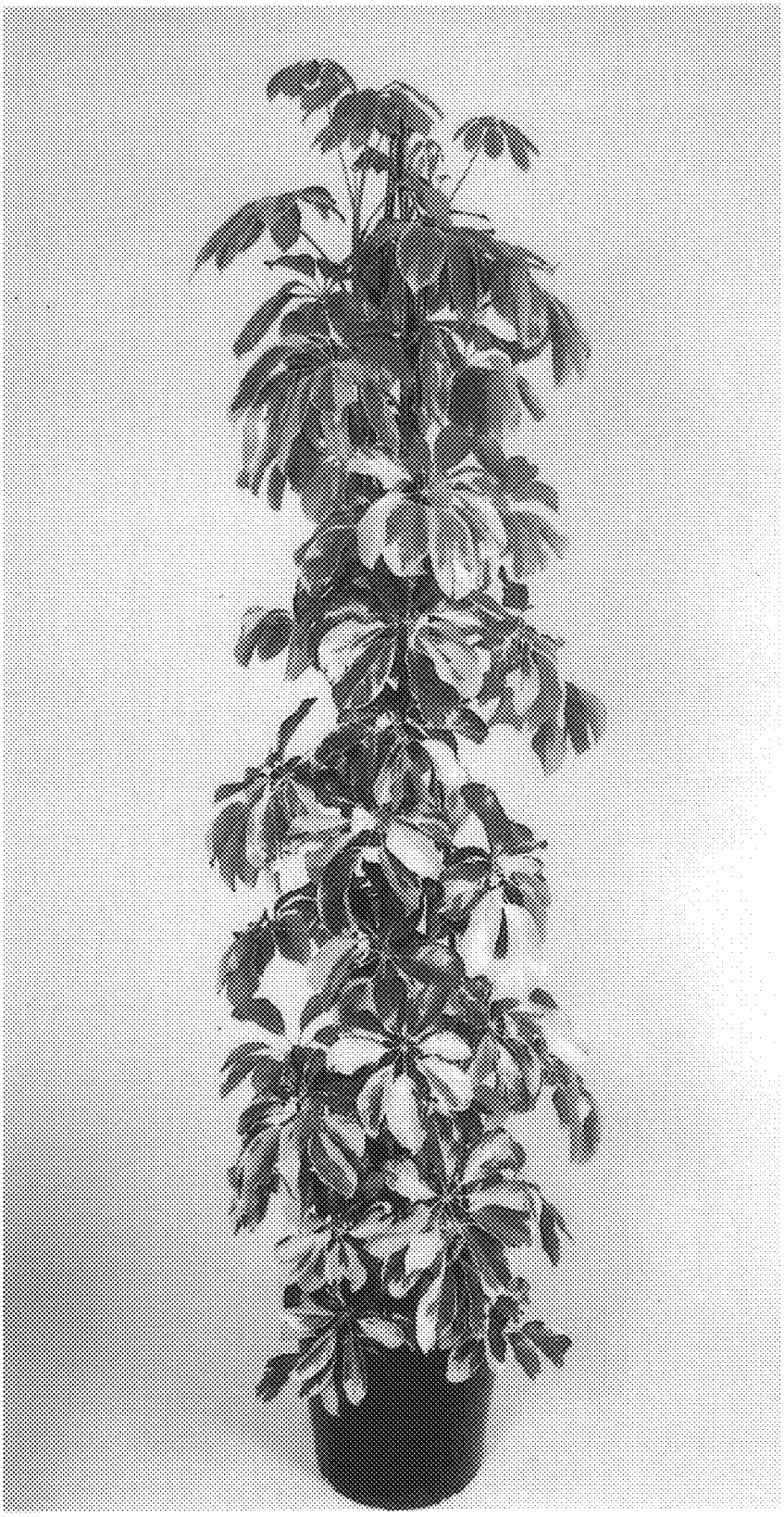

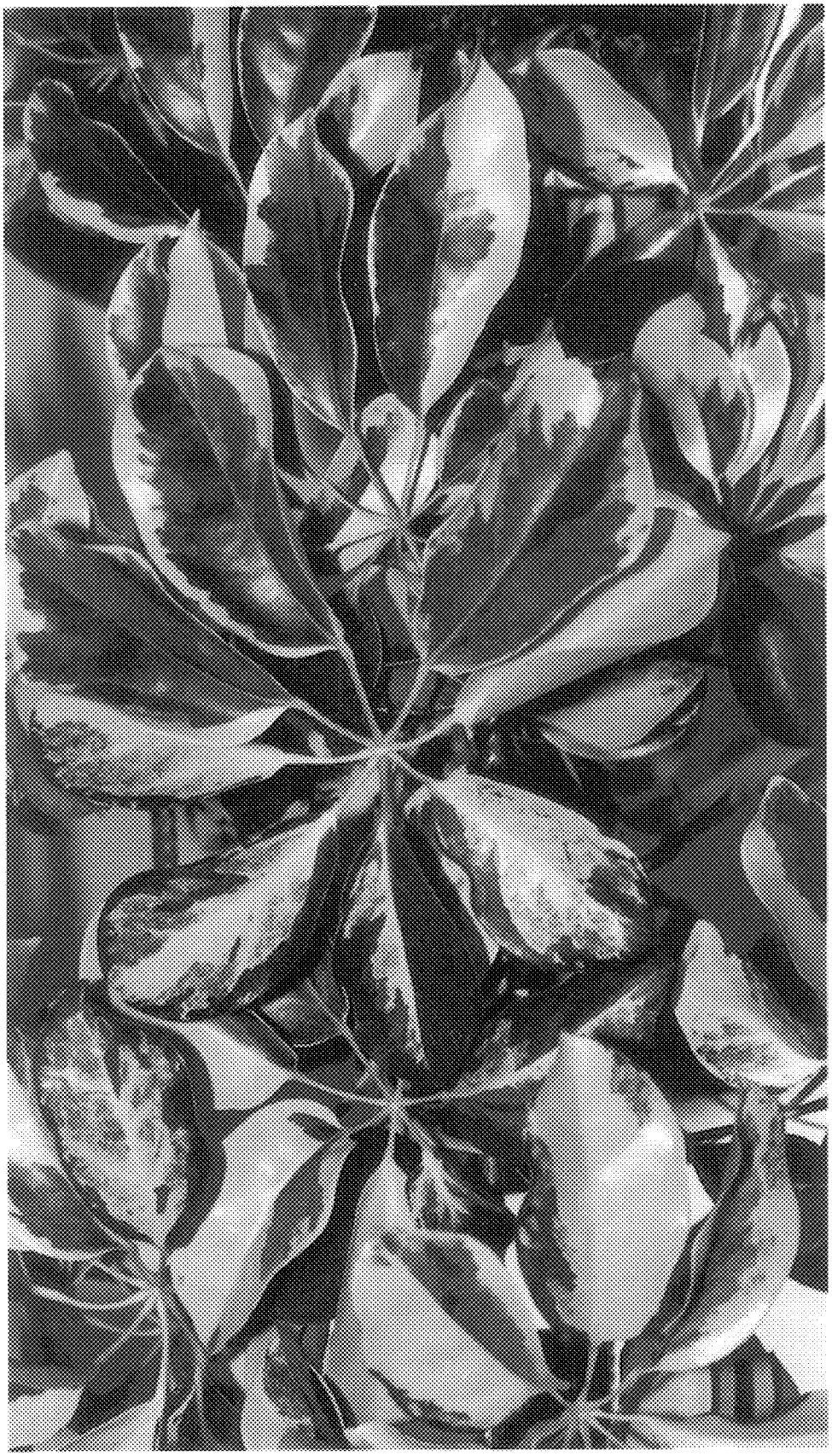

* * * * *